United States Patent [19]

Michelson

[11] 4,400,590
[45] Aug. 23, 1983

[54] APPARATUS FOR MULTICHANNEL COCHLEAR IMPLANT HEARING AID SYSTEM

[75] Inventor: Robin P. Michelson, Redwood City, Calif.

[73] Assignee: The Regents of the University of California, Berkeley, Calif.

[21] Appl. No.: 219,341

[22] Filed: Dec. 22, 1980

[51] Int. Cl.³ .................... H04R 1/22; H04R 25/00
[52] U.S. Cl. ........................... 179/107 FD; 128/784
[58] Field of Search ........ 179/107 R, 107 E, 107 FD, 179/107 BC; 128/789, 784

[56] References Cited

U.S. PATENT DOCUMENTS

| | | | |
|---|---|---|---|
| 3,751,605 | 8/1973 | Michelson | 179/107 R |
| 3,752,939 | 8/1973 | Bartz | 179/107 R |
| 3,818,149 | 6/1974 | Stearns, et al. | 179/107 FD |
| 3,989,904 | 11/1976 | Rohrer et al. | 179/107 FD |
| 4,025,723 | 5/1977 | Blackledge | 179/1 VL |
| 4,063,048 | 12/1977 | Kissiah, Jr. | 179/107 R |
| 4,284,856 | 8/1981 | Hochmair et al. | 179/107 E |

FOREIGN PATENT DOCUMENTS 2823798 9/1979 Fed. Rep. of Germany ...... 128/784

OTHER PUBLICATIONS

"An Eight Channel Scala Tympani Electrode for Auditory Prostheses", by I. J. Hochmair-Desoyer and E. S. Hochmair, *IEEE Transactions on Biomedical Engineering*, vol. BME-27, No. 1, Jan. 1980, pp. 44-50.
White, "The Stanford Artificial Ear Project," *The Stanford Engineer*, Spring/Summer 1980, pp. 3-10.
Merzenich, et al. "Neural Encoding of Sound Sensation Evoked by Electrical Stimulation of the Acoustic Nerve" Reprinted from Annals of Otology, Rhinology and Laryngology, Jul.-Aug. 1973, vol. 82, No. 4, p. 486.
"Report on a Workshop on Cochlear Implants" edited by Michael M. Merzenich, et al. Oct. 23-25, 1974.
Merzenich, et al. "Symposium on Cochlear Implants II. Feasiblity of Multichannel Scala Tympani Stimulation"
Reprint from the Laryngoscope, vol. LXXXIV, No. 11, pp. 1887-1893, Nov. 1974.
Merzenich, "Studies on Electrical Stimulation of the Auditory Nerve in Animals and Man; Cochlear Implants" Human Communication and its Disorders, Raven Press, New York, 1975.
Urban, "Prosthetic Devices", Electrical Stimulation of the Acoustic Nerve in Man—Proceedings of the First International Conference on Electrical Stimulation of the Acoustic Nerve as a Treatment for Profound Sensorineural Deafness in Man, (Merzenich et al. edits., 1974) pp. 179-184.
Bartz, "Prosthetic Devices", Electrical Stimulation of the Acoustic Nerve in Man–Proceedings of the First International Conference on Electrical Stimulation of the Acoustic Nerve as a Treatment for Profound Sensorineural Deafness in Man, (Merzenich, et al. edits. 1974) pp. 185-192.
Schindler, et al. "Multielectrode Intracochlear Implants" Reprint from the Archives of Otolaryngology, Dec. 1977, vol. 103.
Merzenich, et al. "Cochlear Implant—The Interface Problem" Biomedical Engineering & Instrumentation Functional Electrical Stimulation (1977) vol. 3, 321-340.
White, "Design Considerations of a Prosthesis for the Profoundly Deaf" Doctoral Dissertation, Univ. of California at Berkeley, 1978.

*Primary Examiner*—Thomas W. Brown
*Attorney, Agent, or Firm*—Limbach, Limbach & Sutton

[57] ABSTRACT

A hearing aid system using a pre-aligned, multichannel, intra-cochlear electrode array for electrically stimulating predetermined locations of the auditory nerve within the cochlea of the ear with selected frequency components of an external sound signal having magnitudes adjusted according to the requirements of the particular user.

10 Claims, 9 Drawing Figures

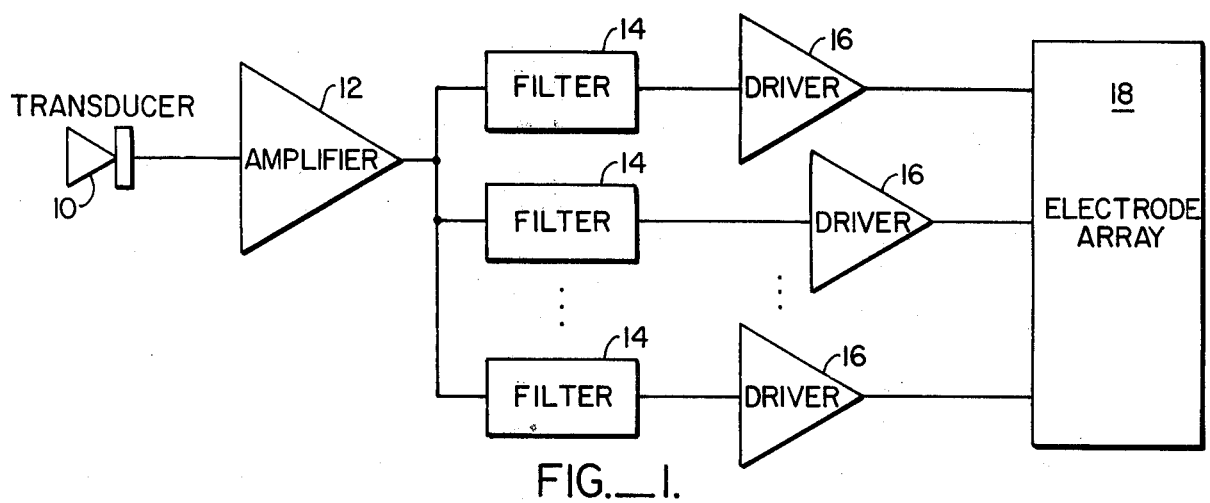
FIG._1.
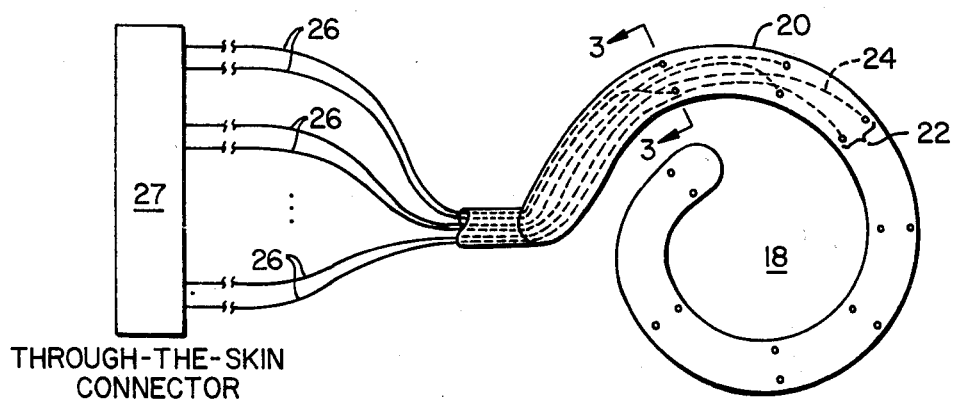
FIG._2.
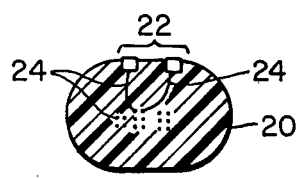
FIG._3.
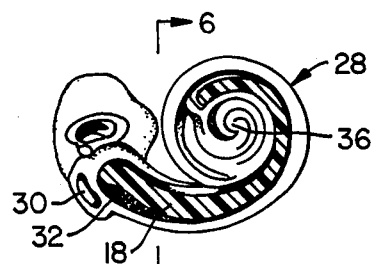
FIG._4.
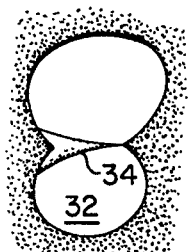
FIG._5.
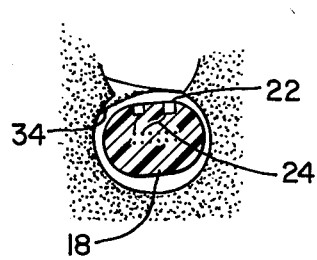
FIG._6.

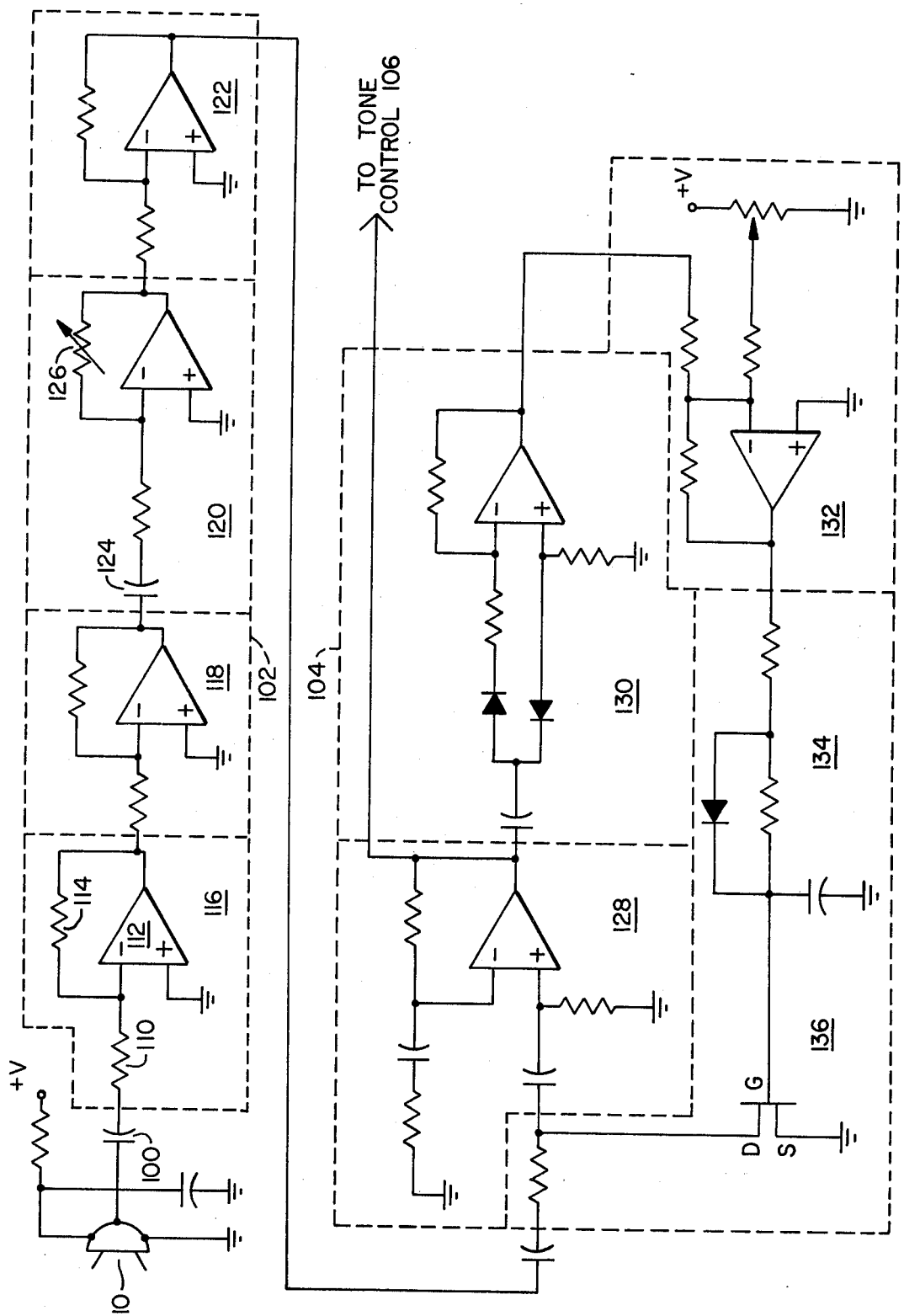
FIG._7A.
FIG._7.

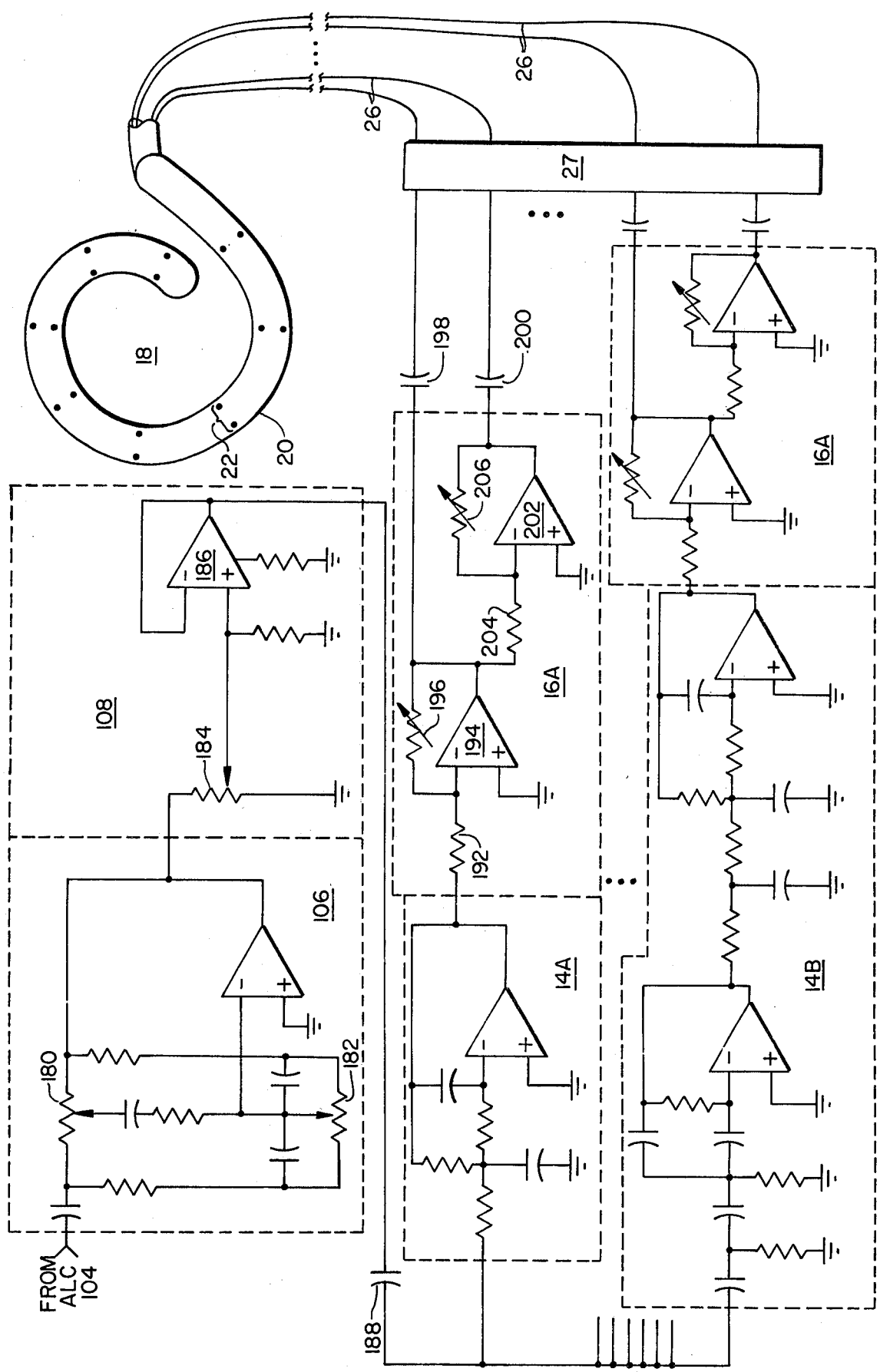
FIG._7B.

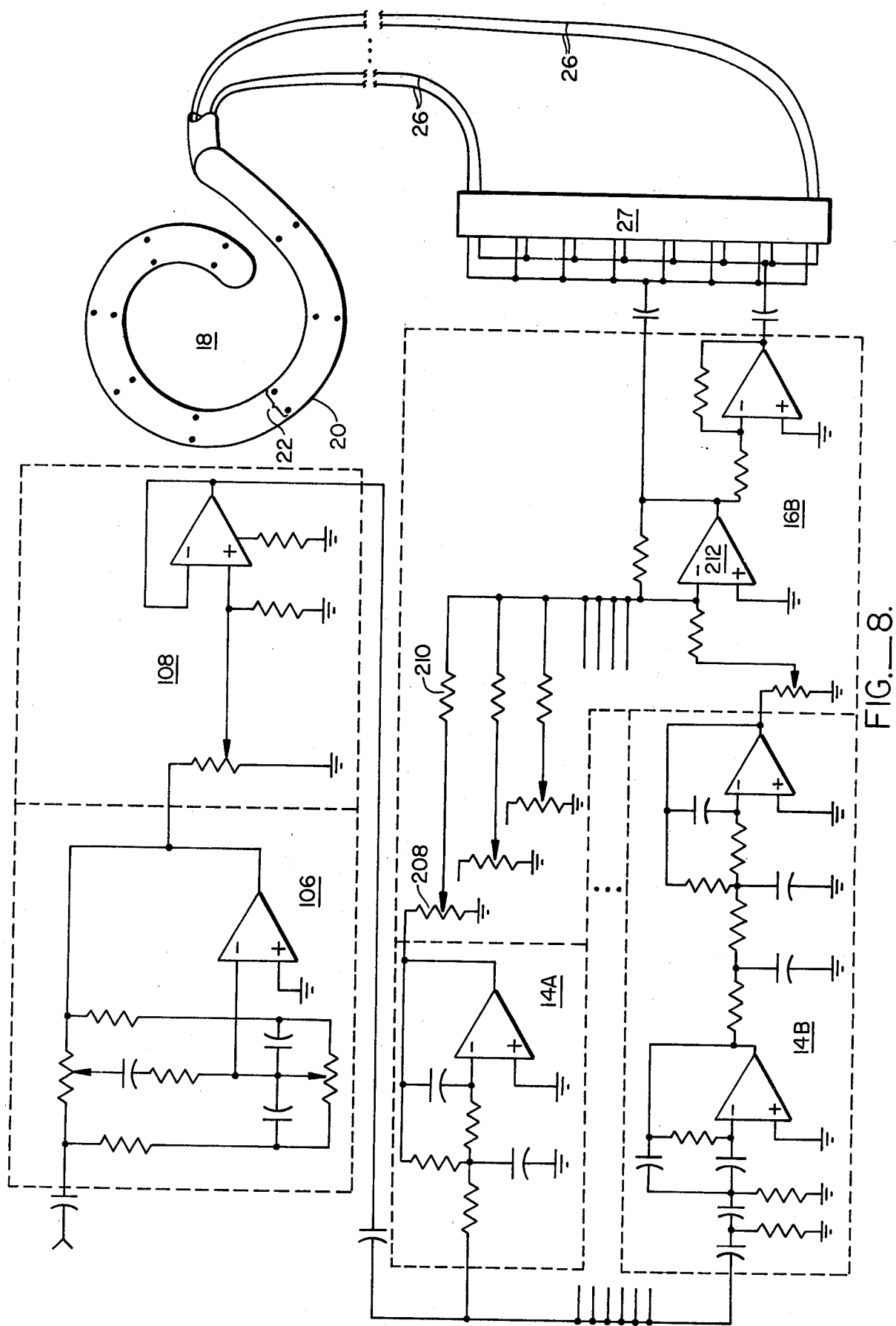
FIG._8.

APPARATUS FOR MULTICHANNEL COCHLEAR IMPLANT HEARING AID SYSTEM

BACKGROUND OF THE INVENTION

The invention is directed to an apparatus for inducing hearing in persons primarily having sensory deafness, but also finds application where conventional hearing aids would normally be effective, but due to reduced hearing sensitivity, additional amplification or bone conduction is useless. Sensory deafness arises when the sensitivity of the cochlea in the internal ear is reduced due to, for example, loss of hair cells, or chemical changes in the perilymph. Reference is made to my U.S. Pat. No. 3,751,605 wherein the phenomena of sensory deafness is described in greater detail.

In the above patent, I disclosed a method for inducing the sensation of intelligible hearing in individuals with sensory deafness by direct electrical excitation of the auditory nerve endings distributed along the basilar membrane within the cochlea. In order to practice the method a bipolar electrode is positioned within the lower scala of the cochlea and a single channel excitation signal is conducted to the electrodes to simulate the naturally generated auditory electric field. The bipolar electrode comprises a pair of conductors running the length of a retaining base member which is resilient and shaped to conform to the inner surface of the lower scala.

While the above method successfully induces the sensation of intelligible hearing in individuals having sensory deafness, the apparatus utilized has produced limited success.

Other attempts at correcting sensory deafness have been directed to implants of electrodes directly into the auditory nerve as opposed to use of an intra-cochlear electrode. Reference is made to Kissiah, Jr. U.S. Pat. No. 4,063,048 wherein single electrodes are implanted in selected locations of the auditory nerve (bypassing a non-functioning cochlea altogether) and are supplied with digitized signal components derived from bandpass filters which filter the electrical analog of the external audio signal into several frequency bands. In Kissiah, it is stated that digitized signals are required because the cochlea does not have the capability to convert analog voltages to digital pulses for stimulation of acoustic nerve endings and, therefore, when analog signals are used the result is severe distortion and lack of fidelity. In addition, it is stated that a major fault of prior devices was the failure to maintain insulation between one implanted electrode and another, especially in intra-cochlear type electrodes where the surrounding cochlear fluid is a non-insulating liquid, thus resulting in stimulation of both intended and non-intended groups of nerve endings.

Contrary to the teachings of Kissiah, and in accordance with the teachings of the present invention, it has been discovered that an apparatus which supplies multichannel analog electrical signals through an intra-cochlear electrode array to nerve endings in the basilar membrane, can be used successfully to induce sensations of intelligible hearing in individuals having sensory deafness.

Experimental results confirm a marked improvement in speech discrimination over the prior art through use of the present invention. When subjects having a single channel electrode apparatus, as described in my prior patent, were compared against those having the multi-channel electrode array system, using a standard Spondee word list, the latter scored 32% while the former did not score above chance. In subsequent experiments with the multichannel electrode array system scores of greater than 50% have been achieved with a standard Spondee word list.

It is believed that these results indicate, for the first time, an unequivocal demonstration of marked improvement of discrimination of speech as a result of using a hearing aid system of the present type.

SUMMARY OF THE INVENTION

The foregoing and other problems of prior art hearing aids for sensory deafness, or where ordinary amplifying hearing aids are unsatisfactory, are overcome by the present hearing aid apparatus adapted for electrical excitation of the cochlea of the ear which comprises transducer means, amplifier means, a plurality of filter means, driver means and a prealigned electrode array. The transducer means convert an external audio signal into an electrical analog signal which is amplified by the amplifier means. The filter means separate the amplified electrical signal into a number of frequency component bands. The frequency components falling within each band can be shaped independently of frequency components falling in other bands. These frequency components are supplied to the drive means which then supply the frequency components to the electrode array. The electrode array is positioned in the cochlea of the ear so that auditory nerve endings in the cochlea in predetermined locations can be electrically stimulated.

Accordingly, it is an object of this invention to provide a multichannel apparatus for intra-cochlear stimulation of auditory nerve endings.

It is a further object of this invention to provide an apparatus capable of producing intelligible discrimination of speech using analog signals to excite an intra-cochlear electrode array.

It is a still further object of the invention to provide an intra-cochlear apparatus wherein frequency components of the applied waveform can be shaped to the requirements of the individual user.

It is another object of this invention to provide an apparatus capable of producing intelligible discrimination of speech using bipolar excitation of the auditory nerve endings.

It is a further object of this invention to provide an apparatus capable of producing intelligible discrimination of speech by exciting specific locations of the cochlea in response to signals supplied from specific frequency bands of the external audio signal.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a simplified functional block diagram of the present invention.

FIG. 2 illustrates a preferred embodiment of the prealigned electrode array.

FIG. 3 illustrates a cross-sectional view of the prealigned electrode array.

FIG. 4 illustrates the positioning of the electrode array within the cochlea of the ear.

FIG. 5 illustrates a cross section of the cochlea.

FIG. 6 illustrates a cross section of the cochlea having a prealigned electrode array positioned therein.

FIG. 7 shows how FIGS. 7A and 7B relate to each other.

FIG. 7A is a detailed schematic transducer, preamplifier, and automatic level control portions of the preferred embodiment of the invention.

FIG. 7B is a detailed schematic of the tone control, user gain control, filtering, and driving circuits, and connector, and prealigned electrode portions of the preferred embodiment of the invention.

FIG. 8 is an alternative embodiment of the invention.

DETAILED DESCRIPTION OF THE PREFERRED EMBODIMENT

Referring more particularly to FIG. 1, a general block diagram of the hearing aid system is shown. A transducer 10 converts external audio signals into analog electrical signals. An amplifier 12 responsive to the analog signals supplies amplified analog signals to a plurality of filters. The filters separate the amplified signals into frequency component bands. These frequency components are then supplied to drivers 16. The frequency components of a particular amplified signal which fall within particular band can then be shaped independently of frequency components falling in other bands by adjusting a gain control within the driver corresponding to the particular frequency band. The drivers then supply electrodes in an intra-cochlear electrode array 18 with the amplified and shaped electrical signals. The intra-cochlear electrode array 18 is shaped so that it can be positioned in the cochlea of the ear so that the electrodes retained by the array will supply electrical excitation to predetermined locations along the auditory nerve in the cochlea.

The method of surgically implanting a parallel-conductor single channel electrode within the cochlea is described in my above-mentioned patent. There, two parallel conductors were imbedded in and retained by a base member having a shape and resiliency as to be suitable for insertion into the cochlea. The conductors extended along the length of the base member.

FIG. 2 illustrates one embodimnet of the multichannel electrode array 18. Like the parallel-conductor electrode, electrodes of the multichannel electrode array 18 are imbedded in and retained by a base member 20 having a shape and resiliency as to be suitable for insertion into the cochlea. Implantation of the electrode array is performed in a similar manner. However, instead of parallel conductors extending the length of the base member, this embodiment of the multichannel electrode array 18 comprises electrode pairs 22 imbedded at selected locations along one face of the base member 20. Conductors 24 running through the interior of the base member 20, see FIG. 3, connect each electrode of the electrode pairs to external leads 26 and thence to a through-the-skin connector 27 for acceptance of electrical signals from the driver circuitry 16. The number and location of the electrode pairs are not intended to be limited by the numbers and locations shown in FIG. 2. In practice, fewer or additional electrode pairs and different electrode pair locations may be satisfactory. In addition, single electrodes located at selected points along the base member can be used, although less advantageously.

In the preferred embodiment, the through-the-skin connector 27 is used to connect the multichannel intra-cochlear electrode array 18 with the remainder of the hearing aid circuitry. Other means of linking the intra-cochlear electrode array 18 with the remainder of the hearing aid circuitry include inductive, as well as radio frequency coupling.

Referring more particularly to FIG. 4, the placement of the multichannel electrode array 18 within the cochlea 28 is illustrated. FIG. 5 illustrates a cross-section of the cochlear 28. In the preferred embodiment, the electrode array 18 is inserted through the round window 30 of the cochlea 28 into the lower scala 32 where it extends along the basilar membrane 34. Auditory nerve endings are distributed along the basilar membrane 34. In my prior patent, I discussed how electrical excitation of the basilar membrane results in the inducement of the sensation of hearing in people suffering from sensory deafness. Place-frequency, first discovered by Von Bekesy, was also discussed to the effect that the nerve endings within the basilar membrane 34 are frequency selective and that nerve endings adjacent the sound window 30 are responsive to high frequencies of the audio spectrum and that the nerve endings become responsive to lower frequencies as the apex 36 of the basilar membrane 34 is approached. Each electrode pair 22 of the multichannel electrode 18 will, therefore, have a position within the lower scala 32 which corresponds to auditory nerve endings which are responsive to a certain band of frequencies. By selecting the positions of the electrodes 22 on the base member 20 the sensation of hearing of predetermined frequency bands may be induced by the application of electrical signals having those frequency components to the corresponding electrodes.

FIG. 6 illustrates a cross section of the multichannel electrode array 18 positioned within the lower scala 32. Also illustrated is the proximity of an electrode pair 22 to the basilar membrane 34 when the array 18 is in place. The result of all of the above is that a prealigned array of electrodes 18 may be constructed so that upon positioning of the array into the lower scala 32 of the cochlea 28, electrodes will be located adjacent predetermined auditory nerve endings in the basilar membrane 34, and that application of electrical signals, having the required frequency component, to the electrodes results in the inducement of the sensation of hearing of the corresponding frequency.

Because the auditory nerve endings are naturally responsive to specific frequencies, depending upon the location of the nerve ending on the basilar membrane 34, so long as the electrical signal applied contains the corresponding frequency, the auditory nerve ending will be stimulated. As a result, the frequency components of electrical signals applied to a particular electrode need not be confined to the frequency band to which the corresponding auditory nerve endings are responsive. However, by confining the frequency components of the excitation signal to the corresponding frequency band, lower thresholds and better defined sensations of hearing may be obtained.

Returning to FIG. 1, the invention will be further described. Transducer 10 converts the external audio signal into its electrical analog. The transducer response is typically flat to 20 KHz.

Amplifier 12 is typically a conventional amplifier, and amplifies the electrical analog signal from the transducer 10.

Filters 14 separate the amplified analog signal from the amplifier 12, into selected frequency bands. The filters 14 may be active filters. Typically, one of the filters is a low pass filter, and the remainder are band pass filters. The center frequencies and bandwidths of these bandpass filters are selected to divide the audio spectrum over a selected frequency range into frequency bandwidths immediately adjacent to each other. By selecting the center frequencies and bandwidths of each filter certain frequencies important to the inducement of the sensation of hearing by stimulating the basilar membrane 34 can be enhanced independently of less important frequencies.

The outputs of the filters 14 are then supplied to drivers 16 which drive the electrodes in the electrode array 18, and also provide means for adjusting the level of amplification provided for each frequency component bandwidth. In this manner, the electrical signal provided to the electrode array can be shaped to the particular requirements of the individual user. It is not necessary for the successful operation of the present invention that each electrode pair receive a specific frequency component band. The combined signal from all of the filters 14 after amplitude adjustment, may be applied to all of the electrodes to produce significant improvement in speech discrimination.

In addition, for the successful operation of the present invention the electrical signals supplied to the electrode array are not required to be digitized, and are most advantageously in analog form.

It is to be understood that the above described elements form the basis of the present invention, and that other elements may be added in combination with the above elements to enhance the operation of the invention, but without departing from the teachings of the invention.

Referring now more particularly to FIGS. 7A and 7B, the preferred embodiment of the invention will be described.

In FIG. 7A, transducer means 10 is a field effect transistor (FET) microphone. The analog electrical signal output from the transducer 10 is capacitively coupled through capacitor 100 to the amplifier means 12.

The amplifier means 12 comprises a four stage preamplifier section 102, an automatic level control circuit 104, a tone control 106, and a user gain control circuit 108.

The four stage preamplifier 102 comprises four inverting amplifiers connected in series. Typical of all amplifiers in the four stage preamplifier section is the first stage 116 which includes a resistor 110 which receives the analog electrical signal from transducer 10 through capacitor 100. The other end of resistor 110 is connected to the inverting input of operational amplifier 112 and one end of feedback resistor 114. The other end of feedback resistor 114 is connected to the output of operational amplifier 112. The non-inverting input of operational amplifier 112 is connected to ground. In this manner, the signal received from the transducer 10 is inverted and amplified by the first stage, with a gain determined by the ratio of resistor 114 to resistor 110.

In like manner, the output of the first stage is supplied to the second stage 118 where the signal is inverted and amplified. The output of the second stage 118 is supplied to the input of the third stage 120, through capacitor 124 which provides low frequency roll-off. Feedback resistor 126 of the third stage 120 comprises a variable resistor which can be adjusted to modify the overall gain of that stage. The output of the third stage 120 is supplied to the input of the fourth stage 122 where it is further inverted and amplified and then supplied to the automatic level control circuit 104.

The automatic level control (ALC) circuit 104 comprises an automatic attenuator circuit (AAC) 136, an amplifier 128, a level detector 130, a summing amplifier 132, and a shaping network 134. The ALC 104 acts to maintain the signal level into the subsequent tone control circuit 106 below a predetermined level. Although ALC 104 is not critical to the proper operation of the present invention, inclusion of the circuit in the amplifier chain provides control over the signal levels in environments where the external sound levels have large variations.

Referring to FIG. 7B, the output of ALC 104 is supplied to tone control circuit 106 which provides separate treble frequency boost or bass frequency boost of the electrical signal. Potentiometer 180 controls the treble response while potentiometer 182 controls the bass response.

The output of tone control 106 is supplied to user gain control 108 which comprises potentiometer 184 and a non-inverting, unity gain amplifier 186. One end of potentiometer 184 is connected to ground while the other end receives the output signal from tone control 106. The wiper of potentiometer 184 is connected to the non-inverting input of unity gain amplifier 186. By adjusting the position of the wiper the resulting voltage divider provides a corresponding fraction of the tone-control signal level to the amplifier 186. The unity gain feature of amplifier 186 is achieved by connecting its output to its inverting input.

In summary, the amplifier means 12 of the preferred embodiment of the invention comprises a four-stage preamplifier section 102 for amplifying the analog electrical signal supplied by the transducer means 10; an automatic level control circuit 104 for maintaining the amplified electrical signal below a predetermined level in environments of widely varying external audio signal levels; a tone control 106 for separate boost of the bass and treble frequencies of the electrical signals; and a user gain control circuit which permits the user to adjust the level of the amplified electrical signal emerging from the amplifier means 12.

The amplified electrical signal output from the amplifier means 12 is coupled to a plurality of filter means 14 through capacitor 188.

In the preferred embodiment, there are eight separate filters, one of which is a low pass filter 14A, with the remaining seven being bandpass filters. In FIG. 7B, circuit 14B illustrates the general form of bandpass filter used; all seven bandpass filters are not shown. In the preferred embodiment, the resistive and capacitive components of the filters are selected to provide filtering over a frequency range up to approximately 10 KHz. The low pass filter 14A filters the low frequency band below 700 Hz. Resistive and capacitive components of the seven bandpass filters are selected so that each of the following bands are filtered: 700 Hz to 1.2 KHz, 1.2 KHz to 1.7 KHz, 1.7 KHz to 2.4 KHz, 2.4 Khz to 3.3 KHz, 3.3 KHz to 4.8 KHz, 4.8 KHz to 6.7 KHz, and 6.7 KHz to 9.5 KHz. The above frequency bandwidths are intended to be illustrative and not a limitation of frequency bands with which the present invention may be implemented.

The frequency component output of each filter 14 is supplied to drivers 16. In the preferred embodiment, individual drivers 16 are supplied for each filter 14.

FIG. 8 illustrates an alternative embodiment in which the outputs of each filter are summed together in a single driver 16B.

In the preferred embodiment, each individual driver means 16 provides a bipolar output signal. The implementation of a typical driver will now be described. The signal from low pass filter 14A, for example, is received by a resistor 192, the other end of which is connected to the inverting input of an operational amplifier 194. Variable feedback resistor 196 is connected between the output and inverting input of operational amplifier 194 to provide gain adjustment for this stage. The non-inverting input is connected to ground. The output of operational amplifier 194 is supplied to one electrode of an electrode pair in the electrode array 18, through capacitor 198. The other electrode of the electrode pair above is supplied the inverted output of operational amplifier 194, through capacitor 200 and an inverting amplifier stage. The inverting stage comprises operational amplifier 202, input resistor 204 and variable feedback resistor 206. The resistor 204 connects the output of operational amplifier 194 to the inverting input of operational amplifier 202. Resistor 206 is connected between the output and the inverting input of operational amplifier 202. In the above manner, each pair of electrodes 22 in the electrode array is supplied with a bipolar signal from a corresponding filter means 14.

The typical driver 16 operates as follows. The first inverting amplifier, for example, operational amplifier 194, inverts the signal from the filter means 14. The inverted signal is then supplied to a second inverting stage, in this example operational amplifier 202, as well as capacitively coupled to one electrode of an electrode pair 22. The second inverting stage inverts the signal from the first inverting stage and thus provides a non-inverted, amplified version of the frequency component signal which is capacitively coupled to the second electrode of the above electrode pair 22. Together, the two inverting stages supply two outputs, each moving in opposite polarity to the other, thereby providing the bipolar signal. Additionally, the levels from a particular filter 14 can be adjusted independently of the other filters by adjusting the corresponding feedback resistors in the driver stage, for example variable feedback resistors 196 and 206.

It is to be understood that while only two filters 14A, 14B and two drivers 16A are shown in FIG. 7B, in practice the actual number of each may be greater.

In an alternative embodiment, see FIG. 8, all electrode pairs are driven from a single bipolar driver 16B. The outputs from all of the filters 14 are summed in the first inverting stage of the driver 16B using potentiometers and summing resistors. For example, the output from low pass filter 14A is applied to one end of potentiometer 208, the other end of which is connected to ground. The wiper of potentiometer 208 is connected to one end of summing resistor 210, the other end of which is connected to the inverting input of operational amplifier 212. The outputs of the other filters are similarly input to the inverting input of operational amplifier 212. Operational amplifier 212 therefore operates as a summing amplifier in addition to its usual inverting amplifier role in the driver 16B. The use of potentiometers, for example potentiometer 208, in the input line to the driver 16B permits the levels from each filter to be adjusted independently of each other by adjustment of the corresponding potentiometer. In this manner, the frequency spectrum supplied to an individual user can be adjusted to fit the particular user's hearing requirements.

A further embodiment of the invention involves a monopolar driver means. That is, in either the summed or multi-channel driver implementations above, the driver means output to each electrode or electrode pair is supplied from a single amplifier output, for example operational amplifier 212, rather than a bipolar pair, for example, operational amplifiers 194 and 202.

Use of a bipolar driver means 16 or, in other words, supplying a bipolar excitation signal to each electrode pair 22 of the electrode array 18, while not necessary to the implementation is nonetheless preferred. When a bipolar excitation signal is used in conjunction with an electrode pair, the excitation signal is only applied to the portion of the auditory nerve between the electrode pair. When a monopolar excitation signal is used with a single electrode the excitation signal stimulates other portions of the auditory nerve endings as well, thus reducing the isolation of the excitation signal to a specific location among the auditory nerve endings.

In the invention either a common or remote ground may be used.

In summary, in the preferred embodiment of the invention, an external audio signal is converted to its electrical analog by FET microphone 10. This electrical analog signal is amplified in a four stage preamplifier 102 and then supplied to an automatic level control means 104 which provides regulation of the amplified signal level supplied to the subsequent stages of the invention. The signal is then supplied to a user tone control circuit 106 and then to a user gain control circuit 108. These two stages permit the user to adjust the level and tone of the amplified signal to his or her individual requirements. The amplified electrical signal output from the user gain adjust circuit 108 is then supplied to a plurality of filter means 14, which separate the amplified signal into a number of frequency component bands. The outputs of each filter means is supplied to a plurality of driver means 16 wherein the signal level from each filter means may be individually adjusted depending upon the hearing requirements of the individual user. The driver means 16 then provide the above frequency component signals to the prealigned electrode array 18, shaped so that it can be implanted in the cochlea of the ear. The prealigned electrode array, upon implant, then applies the frequency component signals to predetermined locations of the basilar membrane to stimulate auditory nerve endings located there.

The terms and expressions which have been employed here are used as terms of description and not of limitations, and there is no intention, in the use of such terms and expressions of excluding equivalents of the features shown and described, or portions thereof, it being recognized that various modifications are possible within the scope of the invention claimed.

What is claimed is:

1. A hearing aid apparatus for electrical excitation of the cochlea of the ear, comprising:
   transducer means for converting an external audio signal into an electrical signal;
   amplifying means responsive to the electrical signal for producing an amplified signal;
   a plurality of filter means responsive to the amplified signal for separating the amplified signal into a plurality of frequency component signals and for selectively shaping the component signals;

driver means responsive to the component signals for amplifying the component signals;

a prealigned array of electrodes responsive to the amplified component signals and positionable within the cochlea of the ear for stimulating nerve endings within the cochlea in predetermined locations.

2. The combination of claim 1 wherein the driver means include a plurality of drivers, each of the drivers having an input connected to the output of a different filter means, and each having an output for supplying designated electrodes of the prealigned electrode array with the amplified component signal.

3. The combination of claim 1 wherein the driver means further comprise summing means for combining component signals supplied from the filter means so that the combination of component signals is supplied to all electrodes of the electrode array.

4. The combination of claim 2 or 3 wherein the driver means provide bipolar component signals to the electrode array.

5. The combination of claim 1 further including automatic level control means interposed between the transducer means and the amplifying means and responsive to the amplified electrical signal to provide limiting of the amplified signal applied to the filter means.

6. The combination of claim 1 wherein the electrode array comprises:
a base member which is contoured to be positionable within the cochlea of the ear;
a plurality of electrodes retained by the base member so that electrode pairs are positioned at predetermined locations along the base member; and
conductor means for supplying the amplified component signals to the electrodes within the electrode array.

7. The combination of claim 1 or 5 further including user tone and gain control means, interposed between the amplifying means and the driver means, and which is responsive to the amplified electrical signal to permit the user to adjust the gain and tone of the hearing aid apparatus.

8. The combination of claim 1 or 2 wherein the electrodes are positioned in the electrode array to stimulate predetermined portions of the auditory nerve which are responsive to the particular component signals supplied to each electrode.

9. A hearing aid apparatus for electrical excitation of the cochlea of the ear, comprising:
transducer means for converting an external audio signal into an electrical signal;
amplifying means responsive to the electrical signal for producing an amplified signal;
a plurality of filter means responsive to the amplified signal for separating the amplified signal into a plurality of frequency component signals and for selectively shaping the component signals;
driver means responsive to the component signals for amplifying the component signals, wherein the driver means further comprise summing means for combining component signals supplied from the filter means; and
a prealigned array of electrodes responsive to the combination of component signals and positionable within the cochlea of the ear for stimulating nerve endings within the cochlea in predetermined locations, and so that the combination of component signals is supplied to all electrodes of the electrode array.

10. The combination of claim 9, wherein the driver means provide bipolar component signals to the electrode array.

* * * * *